US012642665B2

(12) United States Patent
Wiley et al.

(10) Patent No.: US 12,642,665 B2
(45) Date of Patent: Jun. 2, 2026

(54) TALONAVICULAR JOINT PROSTHESIS

(71) Applicant: Best Step Orthopedics LLC, Warsaw, IN (US)

(72) Inventors: Roy C. Wiley, Warsaw, IN (US); Lew C. Schon, Baltimore, MD (US); Malik S. Siddique, Newcastle upon Tyne (GB)

(73) Assignee: Best Step Orthopedics LLC, Warsaw, IN (US)

( * ) Notice: Subject to any disclaimer, the term of this patent is extended or adjusted under 35 U.S.C. 154(b) by 1026 days.

(21) Appl. No.: 17/569,388

(22) Filed: Jan. 5, 2022

(65) Prior Publication Data

US 2022/0211511 A1     Jul. 7, 2022

Related U.S. Application Data

(60) Provisional application No. 63/133,978, filed on Jan. 5, 2021.

(51) Int. Cl.
*A61F 2/42*          (2006.01)
*A61F 2/46*          (2006.01)
(Continued)

(52) U.S. Cl.
CPC .......... *A61F 2/4202* (2013.01); *A61F 2/4606* (2013.01); *A61B 17/1682* (2013.01); *A61F 2002/30125* (2013.01); *A61F 2002/30126* (2013.01); *A61F 2002/30245* (2013.01); *A61F 2002/30253* (2013.01); *A61F 2002/30383* (2013.01); *A61F 2002/30481* (2013.01); *A61F 2002/305* (2013.01);
(Continued)

(58) Field of Classification Search
CPC ........ A61F 2/42; A61F 2/4202; A61F 2/4225; A61F 2002/30125; A61F 2002/30658; A61F 2002/3065–3066; A61F 2002/4207; A61F 2002/4212; A61F 2002/4215–422
See application file for complete search history.

(56) References Cited

U.S. PATENT DOCUMENTS 5,037,440 A * 8/1991 Koenig .............. A61B 17/1659
                                                    623/21.19
6,679,916 B1 * 1/2004 Frankle ................. A61F 2/4081
                                                    623/19.12
(Continued)

OTHER PUBLICATIONS

Notification of Transmittal of the International Search Report and the Written Opinion of the International Searching Authority, or the Declaration dated Apr. 22, 2022 for International Application No. PCT/US2022/011333 (8 pages).

Primary Examiner — Marcia L Watkins
(74) Attorney, Agent, or Firm — TAYLOR & EDELSTEIN, PC

(57) ABSTRACT

A talonavicular joint prosthesis includes a navicular component configured to be implanted in a navicular bone and including a base and a surface having an articulation recess formed therein; and a talar component configured to be implanted in a talus bone and including a bearing section configured to rest within the articulation recess. The talar component and the navicular component are shaped such that, when brought together, there is more conformity between the navicular component and the talar component in a dorsal-plantar plane than in a medial-lateral plane.

19 Claims, 20 Drawing Sheets

(51) Int. Cl.
    *A61B 17/16*         (2006.01)
    *A61F 2/30*          (2006.01)

(52) U.S. Cl.
    CPC ............... *A61F 2002/30621* (2013.01); *A61F 2002/30658* (2013.01); *A61F 2002/30884* (2013.01); *A61F 2002/4207* (2013.01); *A61F 2002/4212* (2013.01)

(56)               References Cited

U.S. PATENT DOCUMENTS

| | | | |
|---|---|---|---|
| 9,474,620 | B2 | 10/2016 | Schon et al. |
| 10,117,749 | B2 | 11/2018 | Goldberg et al. |
| 2005/0229433 | A1 | 10/2005 | Cachia |
| 2017/0056187 | A1* | 3/2017 | Humphrey ............ A61F 2/4014 |
| 2019/0038423 | A1 | 2/2019 | Grotz |
| 2019/0314071 | A1 | 10/2019 | Wahl et al. |
| 2020/0276026 | A1 | 9/2020 | Sanders et al. |

* cited by examiner

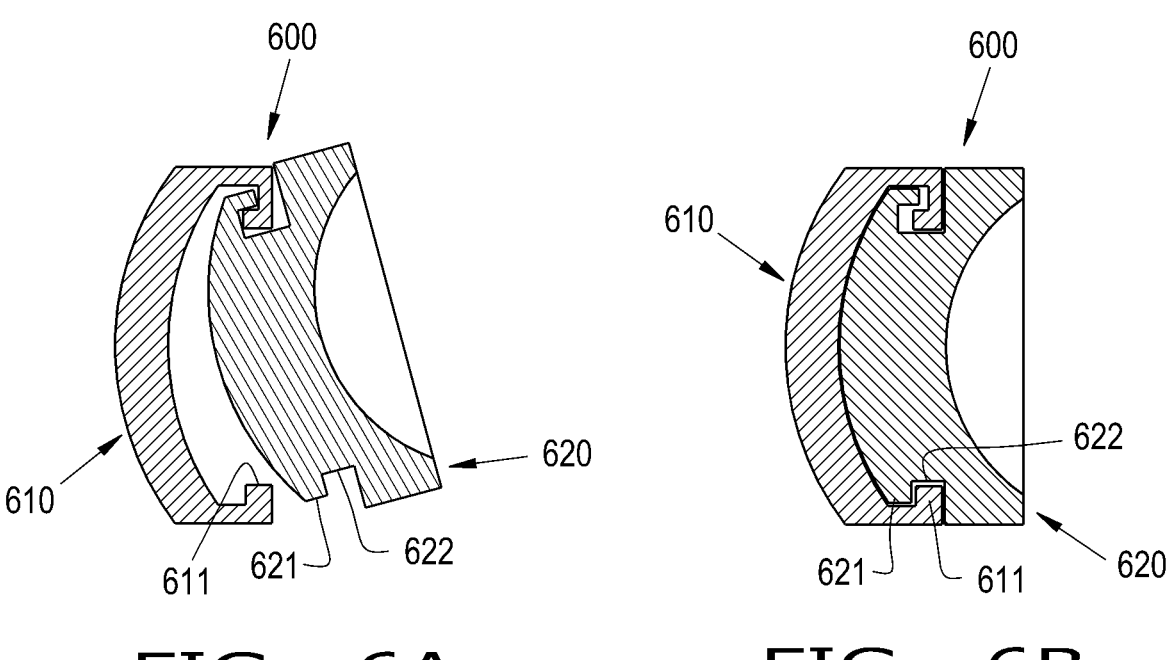
FIG. 6A
FIG. 6B
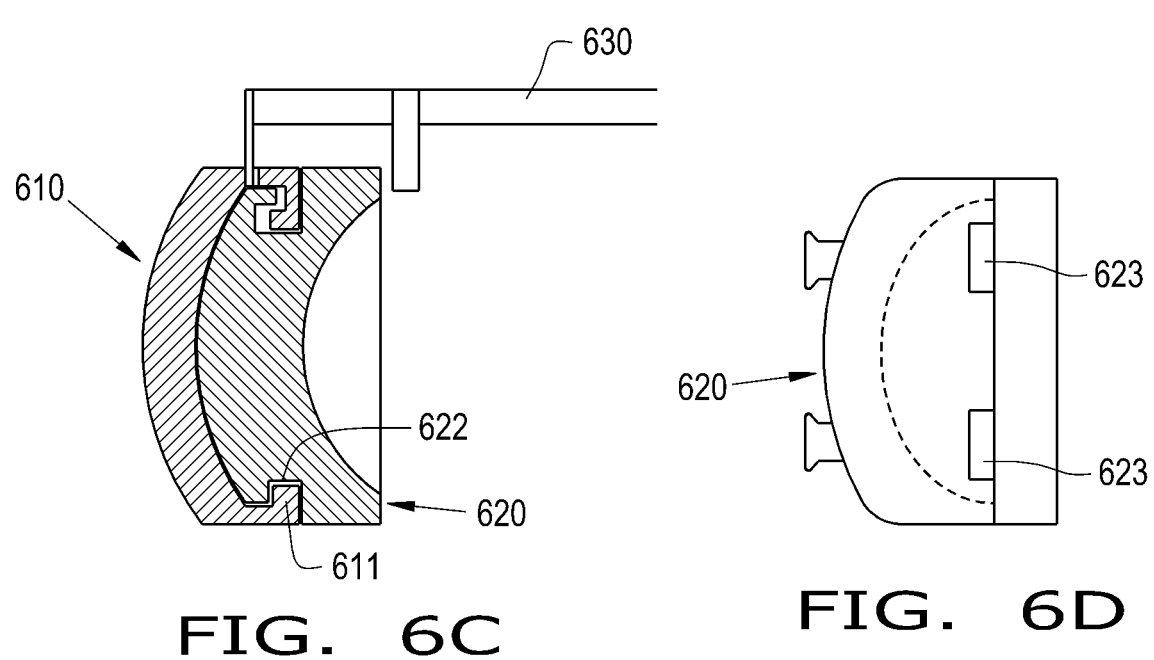
FIG. 6C
FIG. 6D

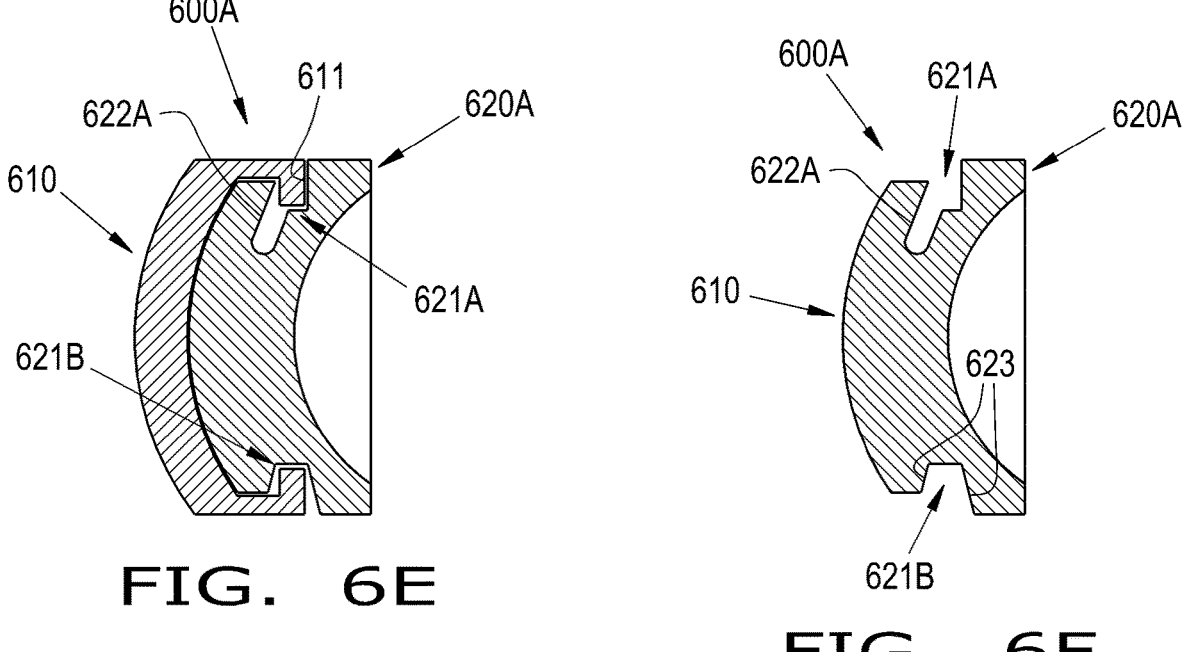
FIG. 6E
FIG. 6F
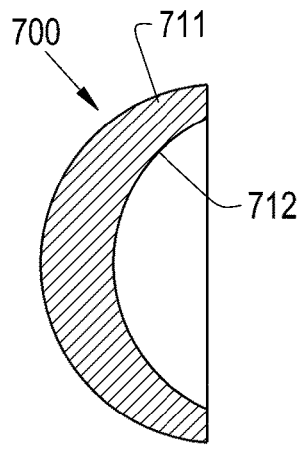
FIG. 7

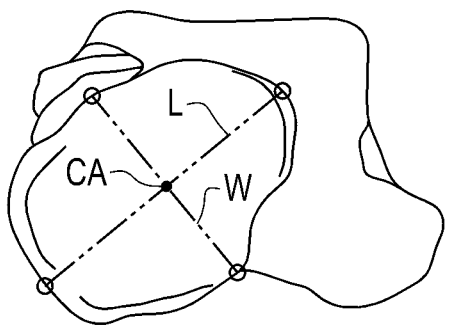
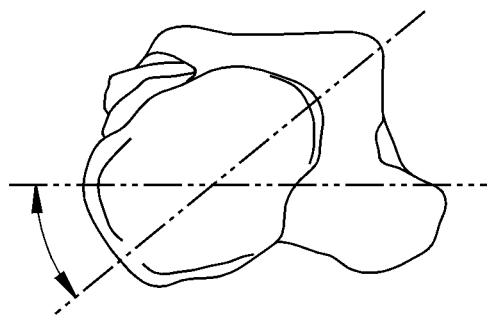
FIG. 9A          FIG. 9B
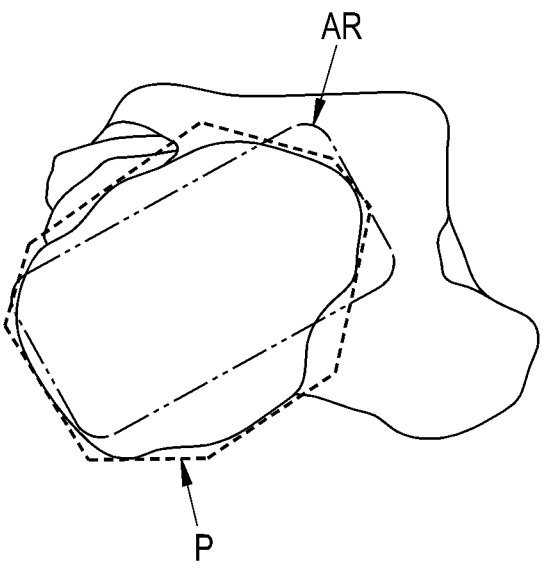
FIG. 10

2400

TALONAVICULAR JOINT PROSTHESIS

CROSS REFERENCE TO RELATED APPLICATIONS

This is a non-provisional application based upon U.S. provisional patent application Ser. No. 63/133,978, entitled "TALONAVICULAR JOINT PROSTHESIS AND METHOD OF IMPLANTING THE PROSTHESIS", filed Jan. 5, 2021, which is incorporated herein by reference.

BACKGROUND OF THE INVENTION

1. Field of the Invention

The present invention is related to orthopaedic prostheses and, more particularly, prostheses for repair and treatment of a talonavicular joint and an associated method of preparing the implantation site and implanting the prosthesis.

2. Description of the Related Art

Disease and damage to bones of the foot, such as the talus and/or the navicular, can severely limit a person's ability to walk. The traditional approach to repairing loss of function is fusing the joint together to stabilize the bones, but this approach limits the range of motion of the foot. More recent treatment approaches have utilized prostheses that are implanted in the foot, but such implants have not, thus far, adequately restored function, such as natural biomechanics of the foot.

What is needed in the art is a talonavicular joint prosthesis that can address some of the issues with known prostheses.

SUMMARY OF THE INVENTION

In accordance with the present invention, a method of replacing the natural talonavicular joint that exists between a patient's talus and navicular bones includes the steps of providing talar and navicular components, surgically preparing the joint surfaces of the patient's talus and navicular bones so as to create a new joint space to accommodate these components, and surgically implanting these components. The implants may be created as a general design and/or patient-specific design utilizing 3D- and/or 4D-imaging and/or a variety of manufacturing techniques including additive manufacturing. 4D-based designs would include the ability to restore specific motion(s) for the patient.

Surgical preparation of the bones is facilitated by establishing a central axis or axes to prepare the joint surfaces from. The central axis (or axes) is defined by either patient specific guides that match the dorsal surface of the talus based on CT, Mill, ultrasound or other imaging modalities, or specific anatomic landmarks of the bones intraoperatively, and an algorithm that is based off of either the navicular or the talar joint surface geometry. The central axis is then mechanically established in the talar bone to guide the preparation of the bone surface, through cutting devices curved in biplanar fashion to minimize the amount of bone removal and match the general curvature of the navicular or talar joint surface.

Alternatively, robotic instrumentation may be utilized to prepare the bone surface using the previously described algorithm, axes, and/or features provided according to the present invention. Exemplary robotic instrumentation includes, but is not limited to, robotic surgical systems such as the da Vinci surgical system.

Alternatively, the cutting guides/central axis can be used to create planar cuts that minimize bone removal based on the arthritic condition of the bone. For instance, the talar surface is typically flattened in arthritic joints so preparation of the bone surface may best be restored by a planar cut defined by the central axis.

The cutting guide/central axis can also establish a way to allow for alignment correction of, or relative to, adjacent bones and provide a way to hold the bones in space during preparation of the navicular or talar joint surface. In addition, they can provide a way to fix the alignment correction through various embodiments of the navicular component, including screws, grafts, wedges or other configurations that replace lost or damaged bone. Modular components can allow for various articular geometries and bone surface geometries to be combined to allow for deformity correction and restoration of motion.

In some embodiments, fixation features, such as pegs, are provided that are designed and located to facilitate dorsal insertion, avoid areas of poor vascularity and have a circular or non-circular geometry to press fit the porous surface into bone prepared via a drill (e.g. round hole) or other cutting tool to create other geometries in the bone.

The design may also avoid interruption of associated joints that are not arthritic or may integrate within the implant (or one or more additional implants) to treat arthritic joints adjacent to the talonavicular joint, such as the subtalar, calcaneal, cuboid, etc.

Features of the design may be applied to, for example, an all-metal talus prosthesis to articulate with one or more of the joints in either hemi-arthroplasty or joint replacement.

In some exemplary embodiments provided according to the present disclosure, a talonavicular joint prosthesis includes a navicular component configured to be implanted in a navicular bone and including a base and a surface having an articulation recess formed therein; and a talar component configured to be implanted in a talus bone and including a bearing section configured to rest within the articulation recess. The talar component and the navicular component are shaped such that, when brought together, there is more conformity between the navicular component and the talar component in a dorsal-plantar plane than in a medial-lateral plane.

In some exemplary embodiments, a method of implanting a talonavicular joint prosthesis in a navicular bone and a talus bone is provided. The method includes: establishing a central axis based on a radius of curvature of the navicular bone in a dorsal view and a width for articulation of the navicular bone, establishing the central axis includes defining at least two arcs from the radius of curvature within the width for articulation and defining a point where the arcs intersect as being on the central axis; aligning at least a portion of a guide with the central axis; preparing the navicular bone and the talus bone using at least one cutting device and the guide to guide movement of the at least one cutting device; and placing a navicular component in the prepared navicular bone and a talar component in the prepared talus bone.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

3

Figure 1:
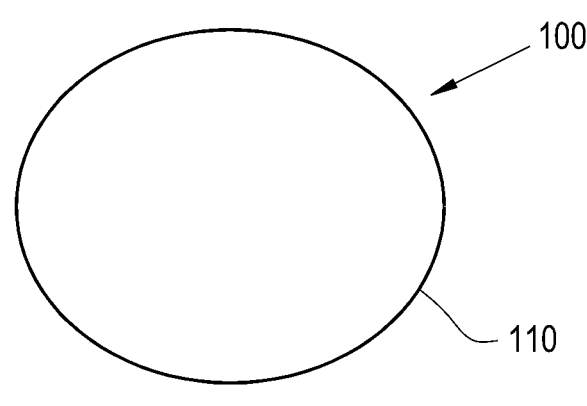
Figure 2:
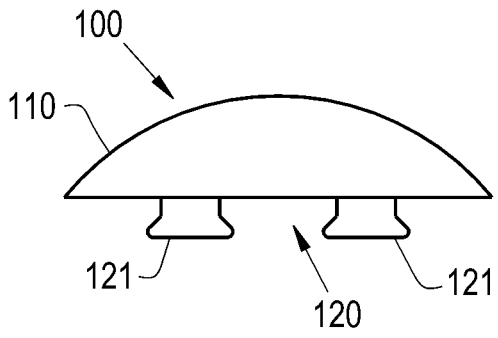
Figure 3A:
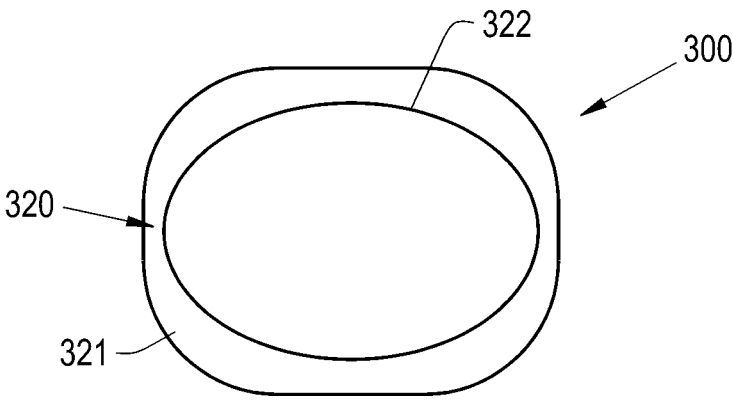
Figure 3B:
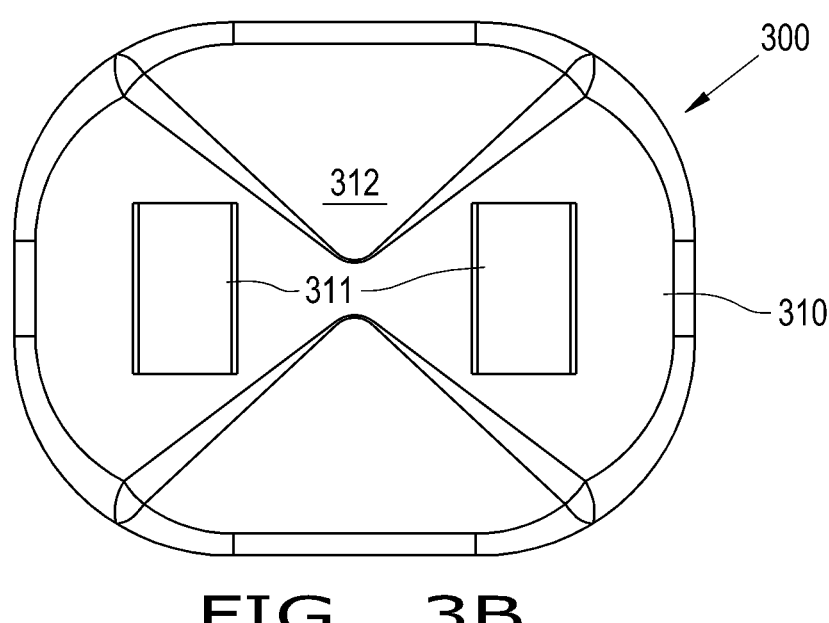
Figure 4:
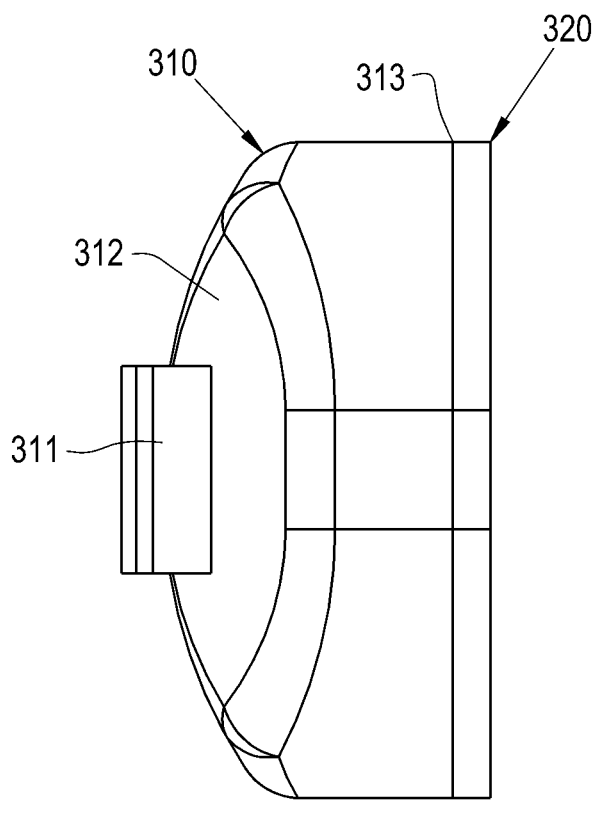
Figure 5D:
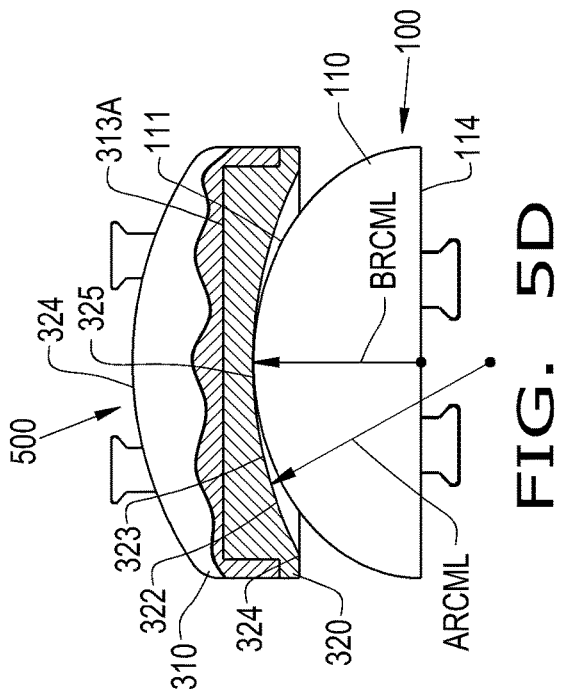
Figure 5C:
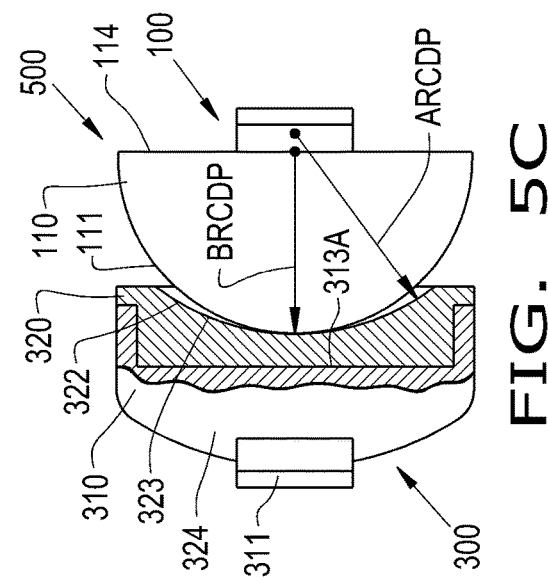
Figure 5A:
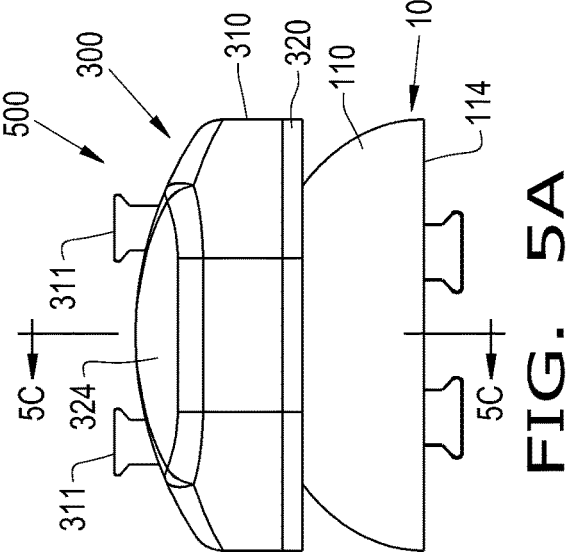
Figure 5B:
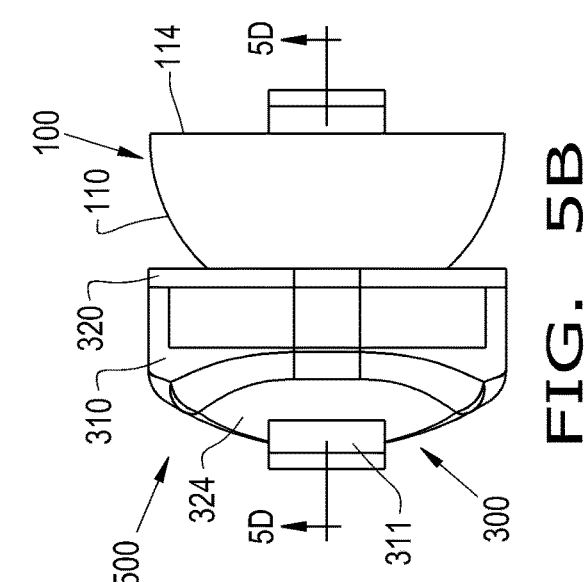
Figure 5E:
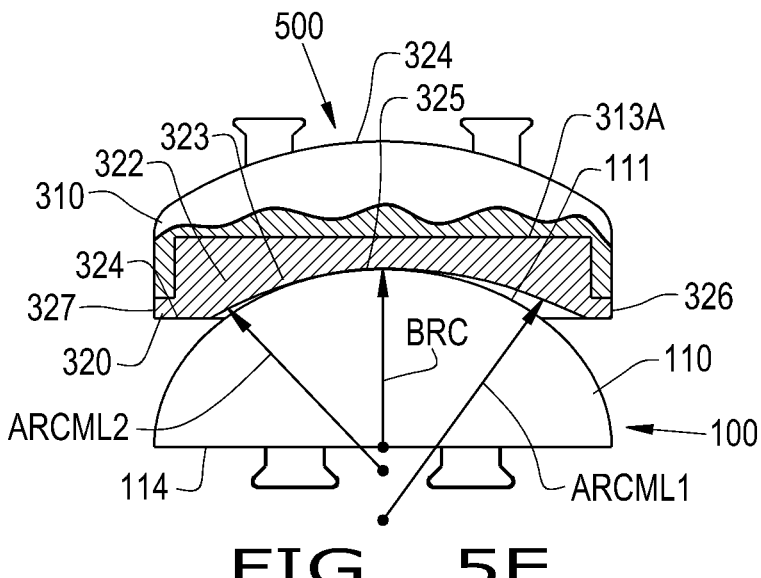
Figure 8A:
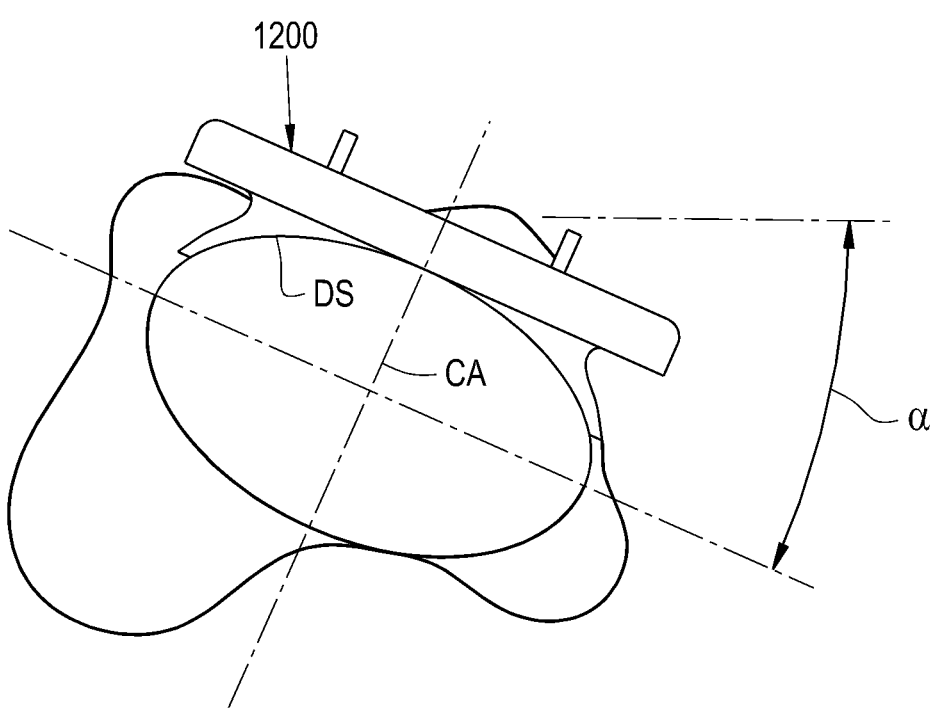
Figure 8B:
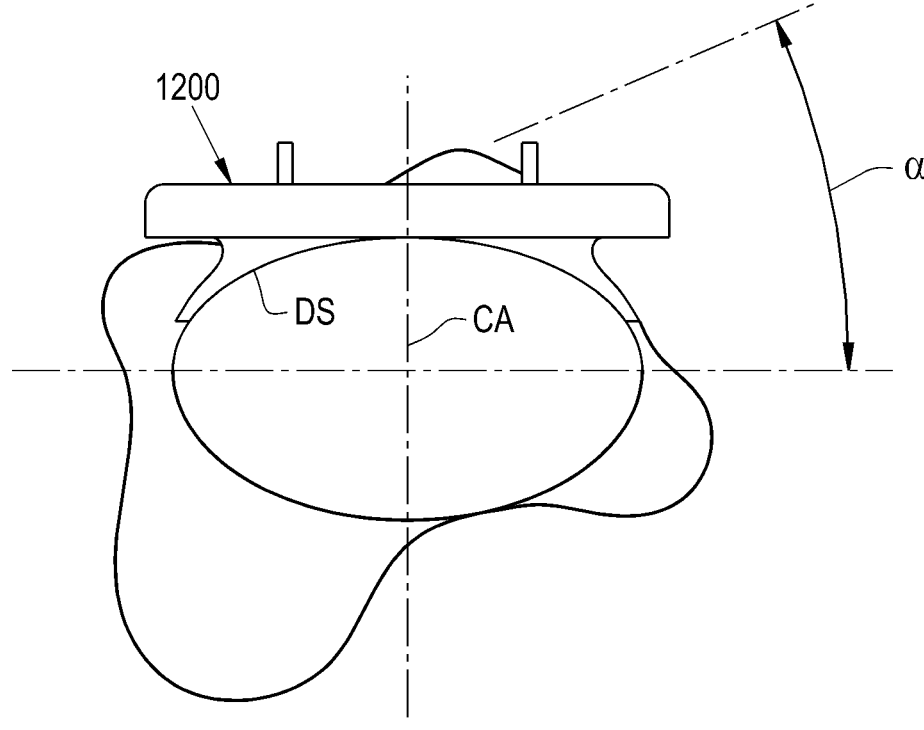
Figure 11:
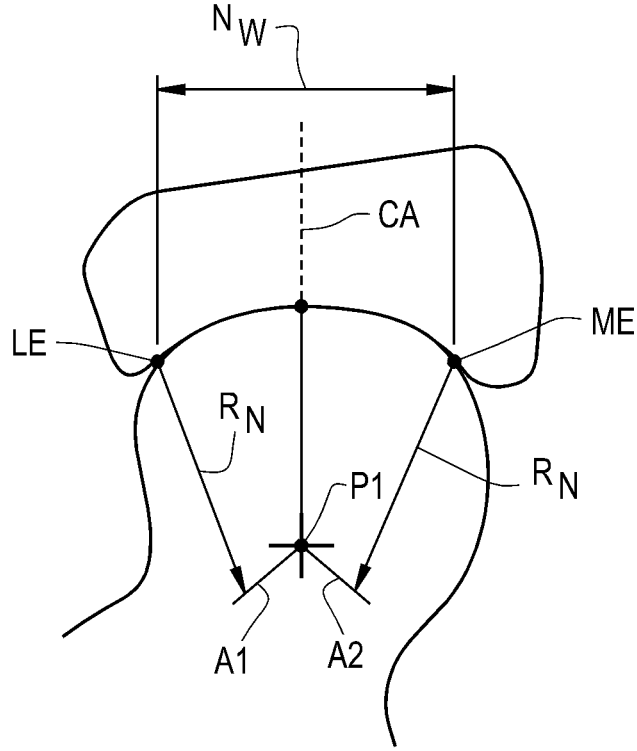
Figure 12:
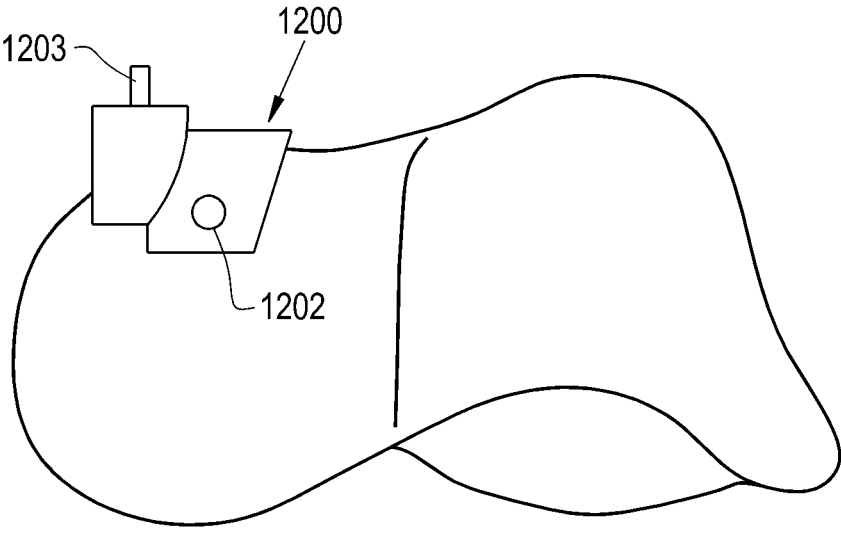
Figure 13:
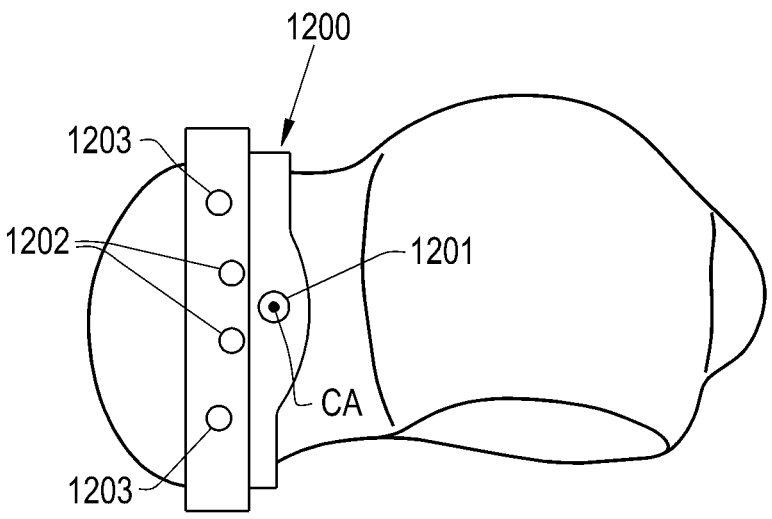
Figure 14:
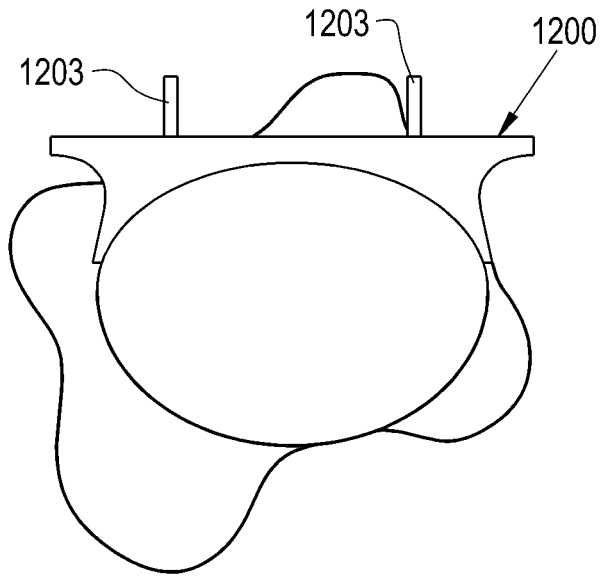
Figure 15:
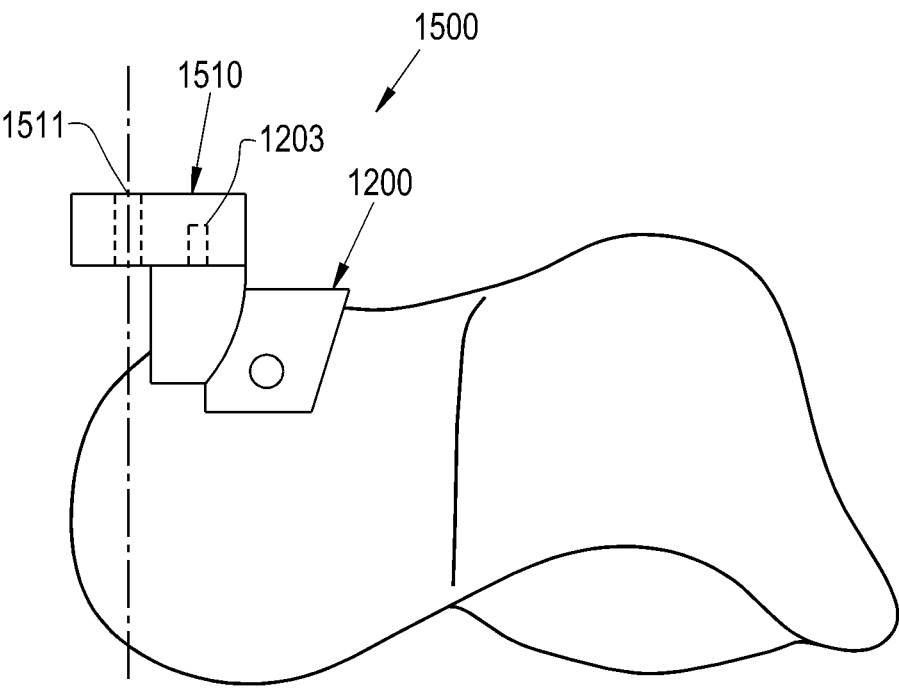

FIG. 1 is a top view of an exemplary embodiment of a talar component of a talonavicular joint prosthesis provided according to the present invention;

FIG. 2 is a side view of the talar component of FIG. 1;

FIG. 3A is a top view of an exemplary embodiment of a navicular component of a talonavicular joint prosthesis provided according to the present invention;

FIG. 3B is a bottom view of the navicular component of FIG. 3A;

FIG. 4 is a side view of the navicular component of FIGS. 3A and 3B;

FIG. 5A is a side view of an exemplary embodiment of a talonavicular joint prosthesis including the talar component of FIGS. 1-2 and the navicular component of FIGS. 3A-4;

FIG. 5B is another side view of the talonavicular joint prosthesis of FIG. 5A;

FIG. 5C is a cross-sectional view of the talonavicular joint prosthesis of FIG. 5A taken along line 5C-5C;

FIG. 5D is a cross-sectional view of the talonavicular joint prosthesis of FIG. 5B taken along line 5D-5D;

FIG. 5E is a cross-sectional view of another exemplary embodiment of a talonavicular joint prosthesis with a talar component and a navicular component that have differing conformities in a medial-lateral plane;

FIG. 6A illustrates an exemplary embodiment of a modular navicular component provided according to the present invention with an articulating section partially coupled to a base;

FIG. 6B illustrates the articulating section inserted in the base of FIG. 6A;

FIG. 6C illustrates an instrument being used to lock together the articulating section and the base of the navicular component of FIGS. 6A-6B;

FIG. 6D illustrates the navicular component of FIGS. 6A-6C with slots that can be used to remove the articulating section from the base;

FIG. 6E illustrates another exemplary embodiment of a modular navicular component provided according to the present invention with an articulating section coupled to a base;

FIG. 6F illustrates the articulating section of the modular navicular component of FIG. 6E by itself;

FIG. 7 is a cross-sectional view of an exemplary embodiment of a modular talar component provided according to the present invention;

FIG. 8A illustrates an exemplary embodiment of a guide provided according to the present invention that is coupled to a talus bone;

FIG. 8B is another view of the guide illustrated in FIG. 8A;

FIG. 9A is an illustration of an image of a talus bone;

FIG. 9B is an illustration of another image of the talus bone of FIG. 9A;

FIG. 10 is an illustration of the talus bone illustrated in FIGS. 9A and 9B with a perimeter and area of the talar head defined;

FIG. 11 illustrates how a central axis may be established according to the present invention;

FIG. 12 is a side view of the guide of FIGS. 8A and 8B aligned with a central axis defined according to the present invention;

FIG. 13 is another view of the guide of FIG. 12;

FIG. 14 is another view of the guide of FIGS. 12-13;

FIG. 15 is a side view of an exemplary embodiment of a cutting guide assembly provided according to the present invention that includes the guide of FIG. 12 aligned with the

Figure 16:
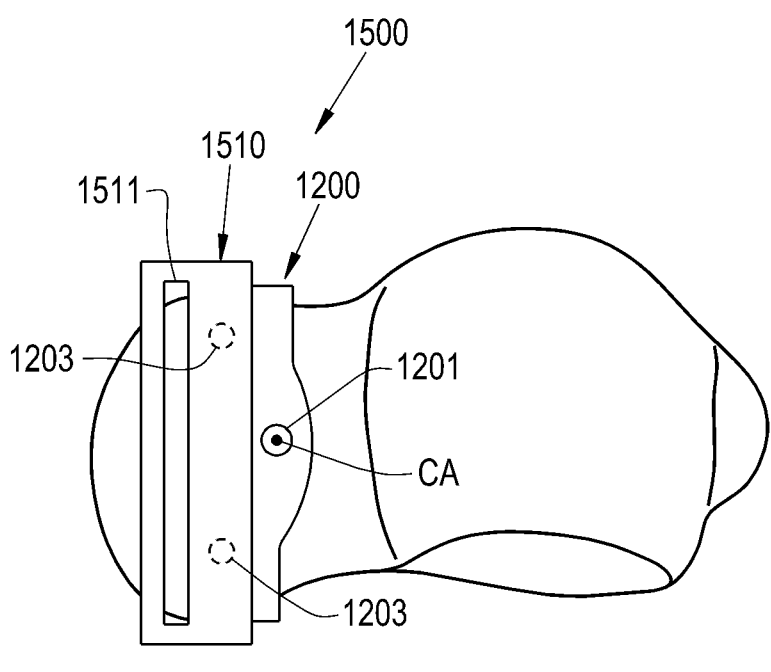
Figure 17:
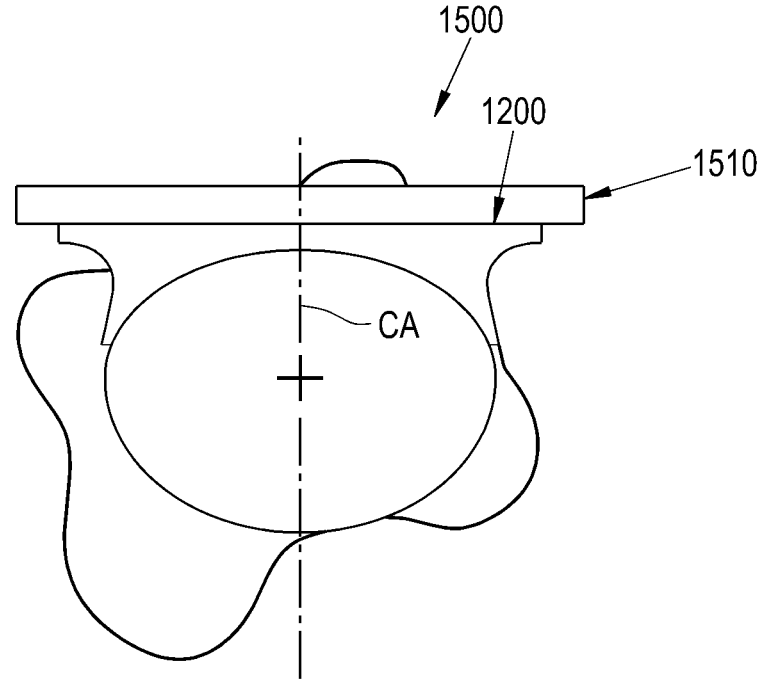
Figure 18:
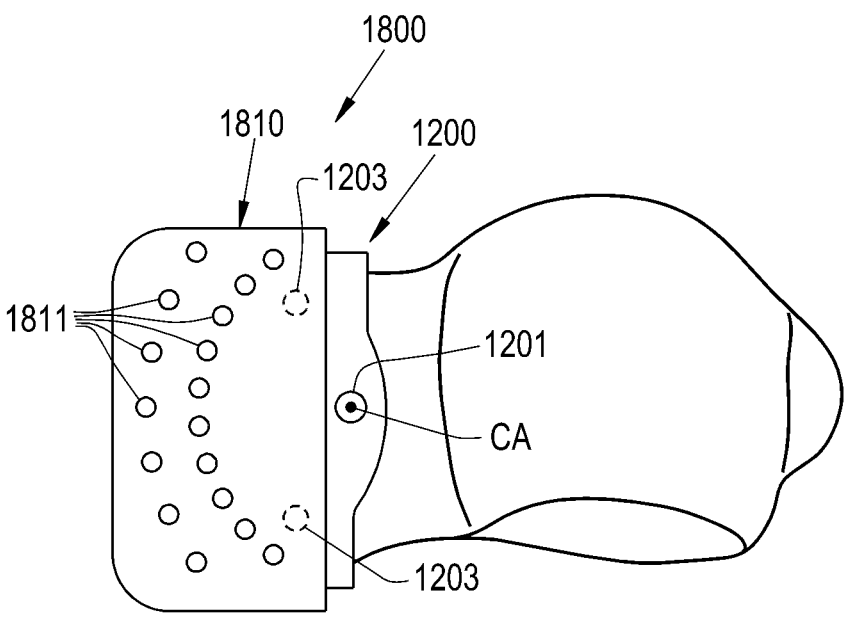
Figure 19:
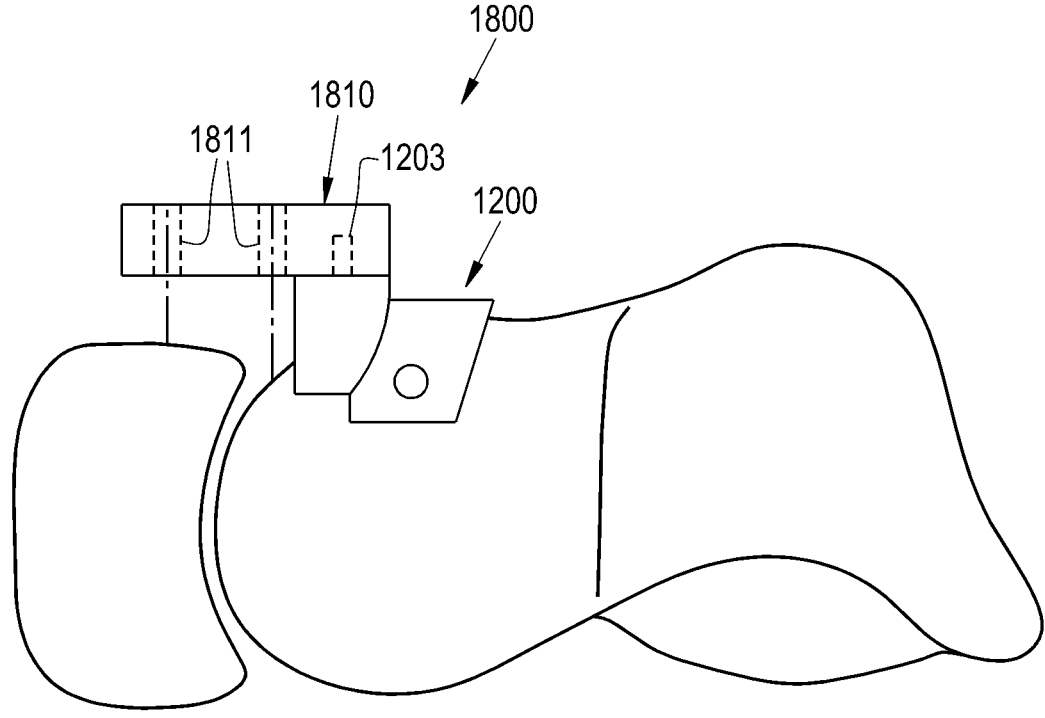
Figure 20:
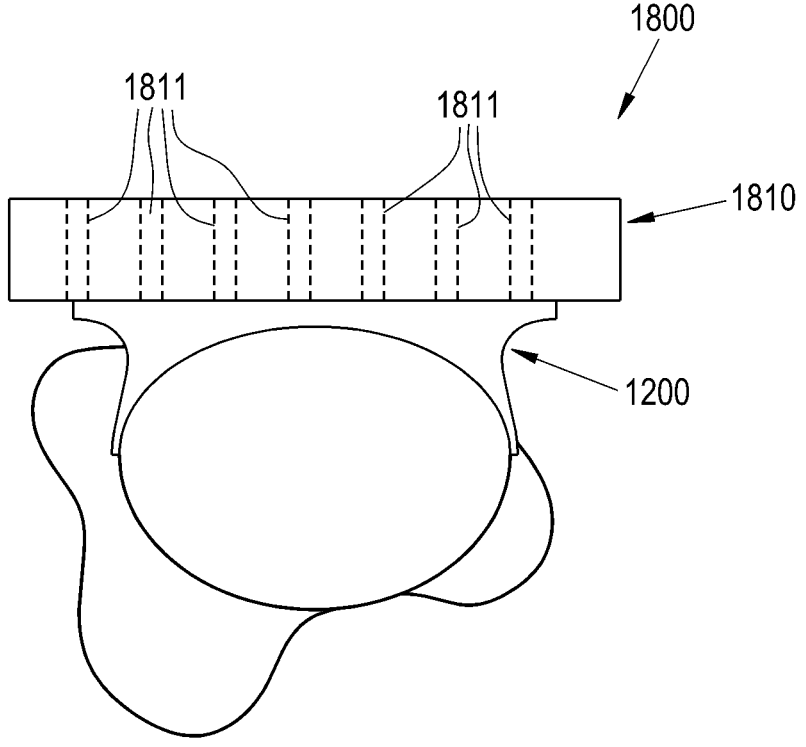
Figure 21A:
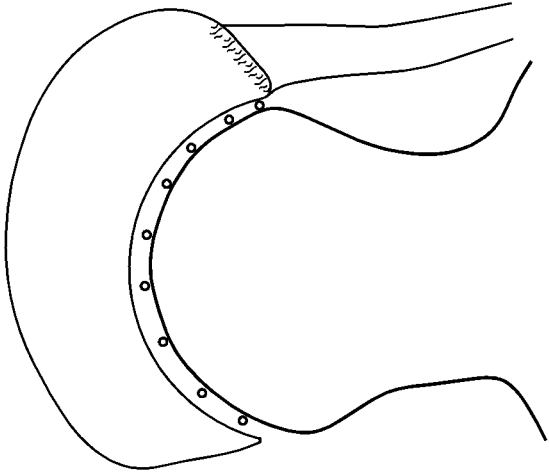
Figure 21B:
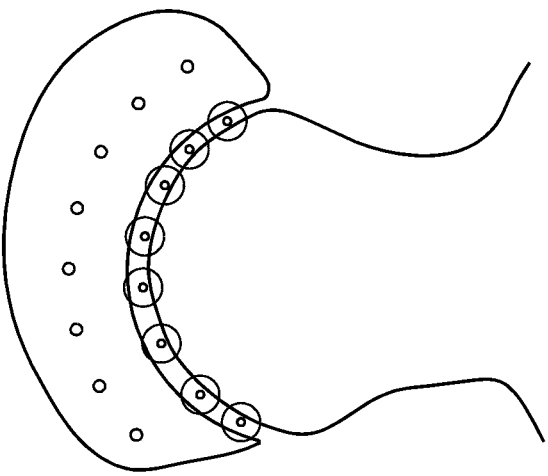
Figure 22A:
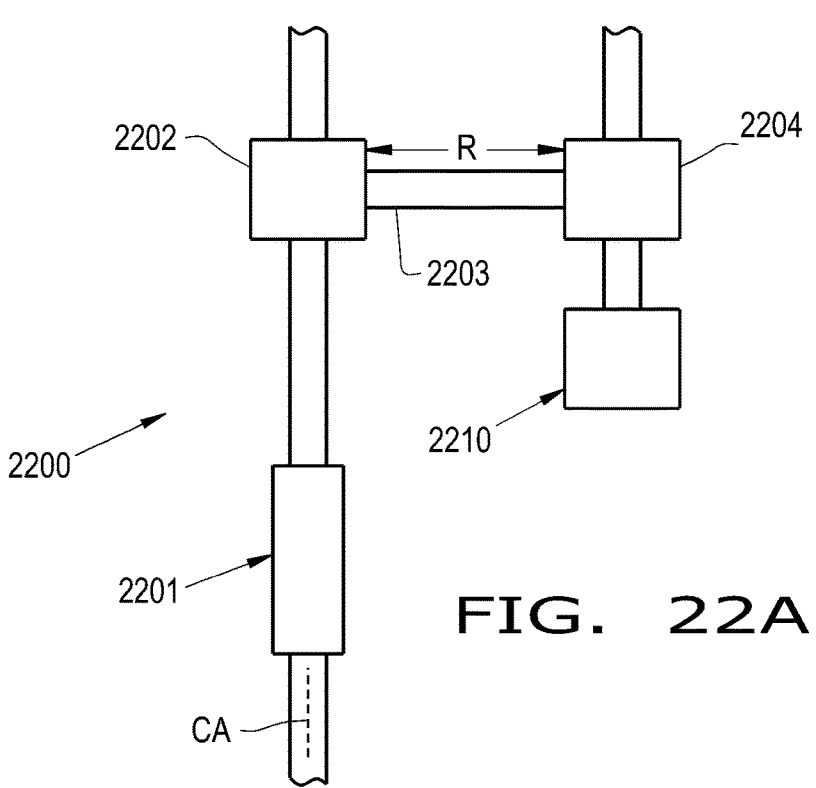
Figures 22B, 22C:
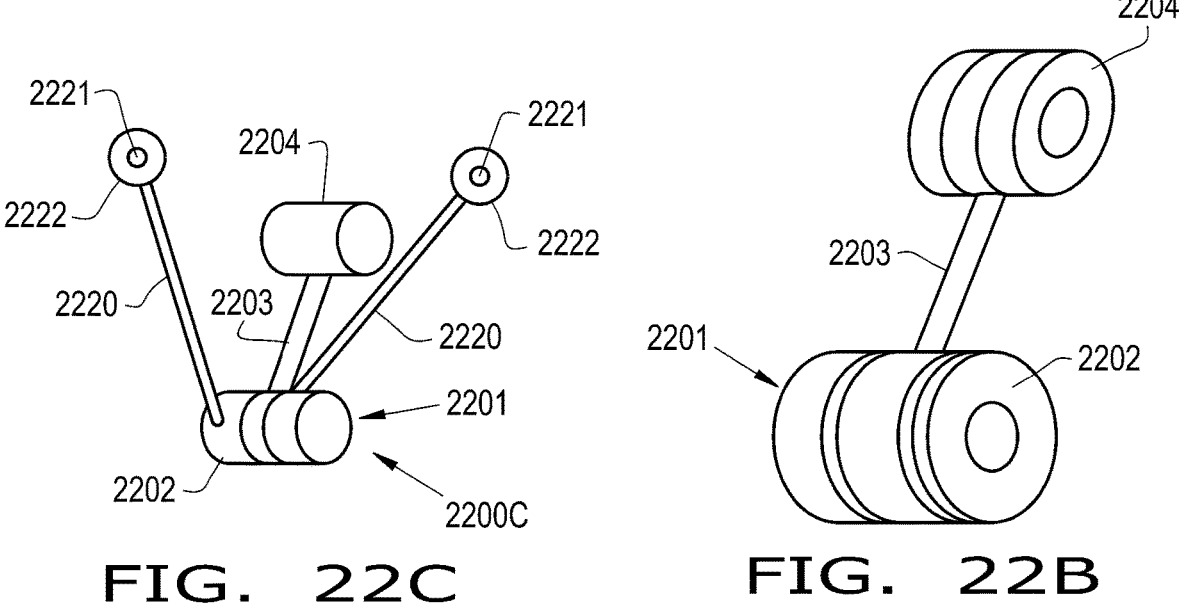
Figure 23A:
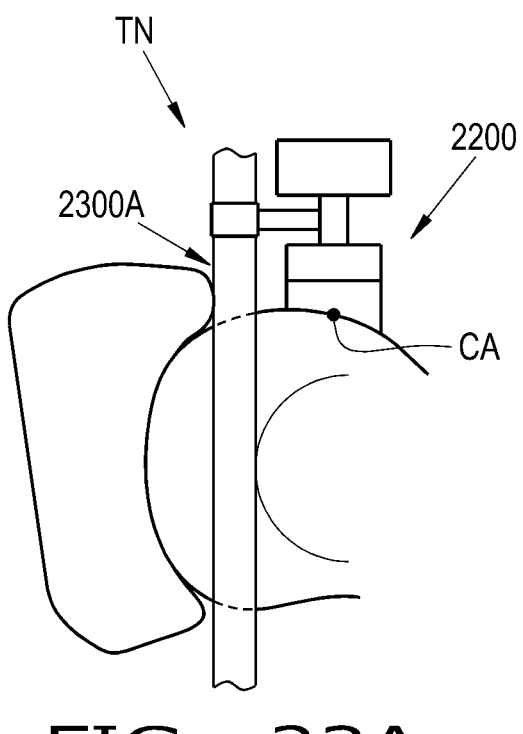
Figure 23B:
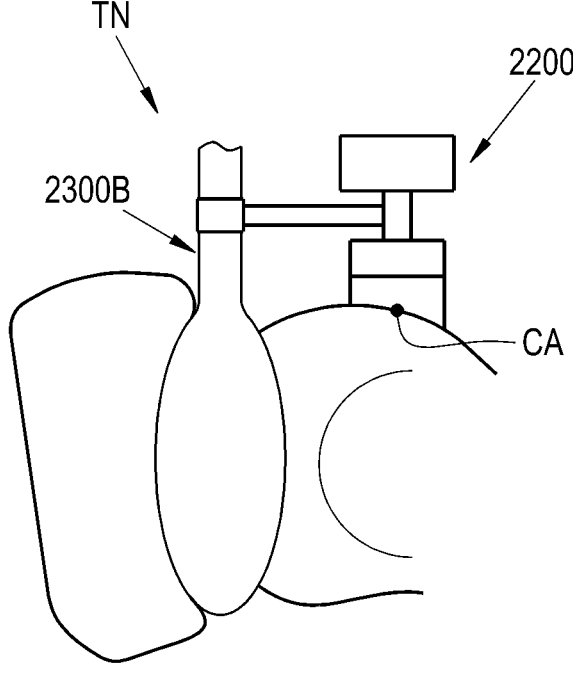
Figure 24:
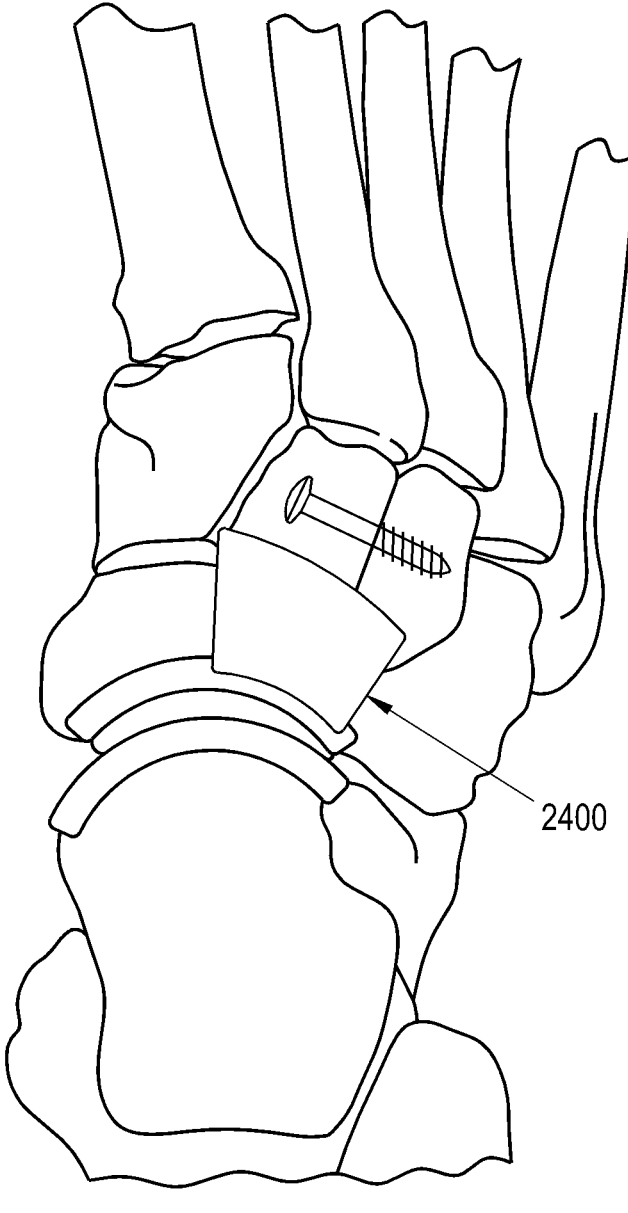
Figure 25A:
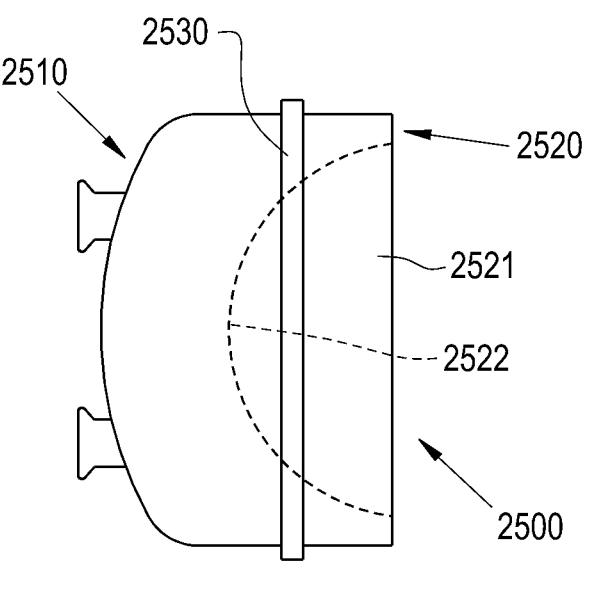
Figure 25B:
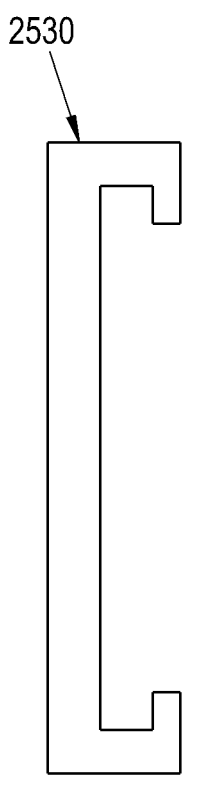
Figure 25C:
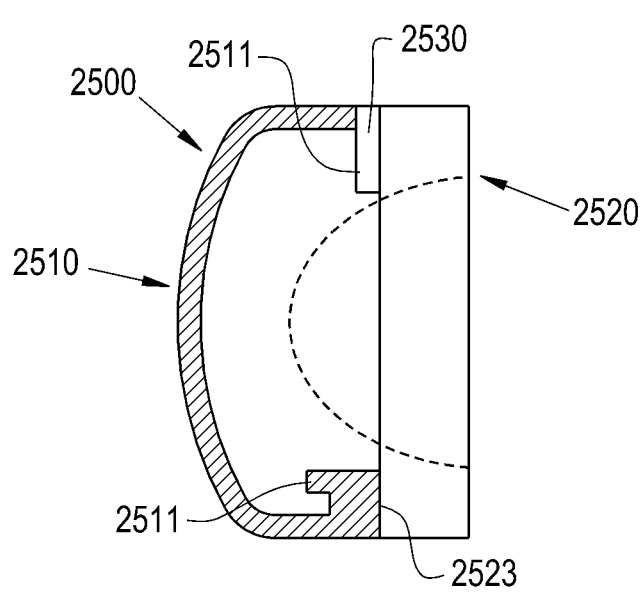
Figures 26A, 26B:
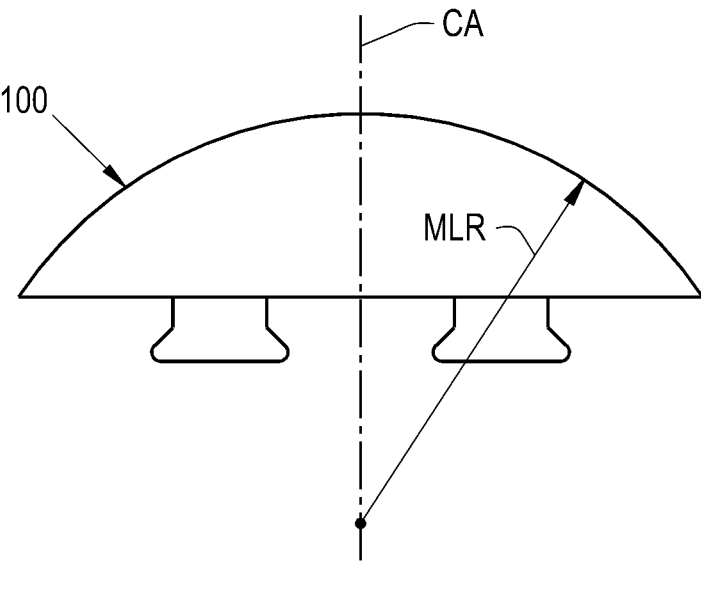

4 central axis defined according to the present invention and a cutting guide coupled to the guide;

FIG. 16 is another view of the cutting guide assembly of FIG. 15;

FIG. 17 is another view of the cutting guide assembly of FIGS. 15-16;

FIG. 18 is a top view of an exemplary of a drill guide assembly provided according to the present invention that includes the guide of FIG. 12 aligned with the central axis defined according to the present invention and a drill guide coupled to the guide;

FIG. 19 is a side view of the drill guide assembly of FIG. 18;

FIG. 20 is another view of the guide of FIGS. 18-21;

FIG. 21A illustrates drill holes formed in a bone using the drill guide assembly of FIGS. 18-20;

FIG. 21B illustrates a cutting device connecting the drill holes formed in the bone of FIG. 21A and creating a mating surface for bone;

FIG. 22A illustrates an exemplary embodiment of a cutting device assembly and a cutting device that may be used to connect the drill holes illustrated in FIGS. 20A-20B;

FIG. 22B illustrates another view of the cutting device assembly and cutting device illustrated in FIG. 22A;

FIG. 22C illustrates another exemplary embodiment of a cutting device assembly that may be used to connect the drill holes illustrated in FIGS. 20A-20B, the cutting device assembly having fixation arms that may be pinned to one or more adjacent bones;

FIG. 23A illustrates a side view of a step of preparing a talonavicular joint to accept a joint prosthesis using a cutting device in the embodiment of a cylindrical mill;

FIG. 23B illustrates a side view of another step of preparing the talonavicular joint of FIG. 23A to accept a joint prosthesis using a curved mill;

FIG. 24 illustrates a cross-sectional view of another exemplary embodiment of a talonavicular joint prosthesis provided according to the present invention that includes a wedge implanted in a foot;

FIG. 25A illustrates another exemplary embodiment of a modular navicular component provided according to the present invention with a base that is configured to be locked to an articulating component by a locking clip;

FIG. 25B illustrates an exemplary embodiment of a locking clip that may be used to lock the base and articulating component of FIG. 25A together;

FIG. 25C illustrates the locking clip of FIG. 25B locking together the base and articulating component of FIG. 25A together;

FIG. 26A illustrates a medial-lateral radius of the talar component of FIGS. 1-2 by itself when aligned along the central axis defined according to the present invention; and FIG. 26B illustrates a dorsal-plantar radius of the talar component of FIGS. 1-2.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Referring now to the drawings, and more particularly to FIGS. 1-5D and 26A-26B, there is shown an exemplary embodiment of a talonavicular joint prosthesis 500 (illustrated in FIGS. 5A-5D) which generally includes a talar component 100, illustrated by itself in FIGS. 1-2 and 26A-26B, and a corresponding navicular component 300, illustrated by itself in FIGS. 3A-4, that are configured to be implanted at a prepared talonavicular site, i.e., in a prepared talus bone and a prepared navicular bone, respectively. The components 100, 300 both comprise one or more biocompatible materials that are suitable for implantation in an anatomical space. Exemplary materials include but are not limited to: biocompatible metals such as titanium, cobalt-chrome, tantalum, and stainless steel; and polymers such as ultra-high molecular weight polyethylene (UHMWPE), polyaryl ether ketones (PAEK) such as polyether ether ketone (PEEK), polylactic acid (PLA), and polyglycolic acid (PGA). In some embodiments, the components 100, 300 are formed with different materials. For example, the talar component 100 may comprise a cobalt chrome molybdenum alloy that is plasma sprayed with titanium and coated with hydroxyapatite while the navicular component 300 comprises a titanium base 310 and a UHMWPE articulating surface 321. It should be appreciated that a wide variety of materials may be used to form the components 100, 300 of the talonavicular joint prosthesis 500, with the previously described materials being exemplary only. In some embodiments, portions of the components 100, 300 may be non-porous, i.e., have a porosity of less than 5%, to prevent significant tissue ingrowth therein and other portions may be highly porous, i.e., have a porosity greater than 40%, to encourage tissue ingrowth therein.

Referring specifically to FIGS. 1-2 and 26A-26B illustrating the talar component 100, it can be seen that the talar component 100 has a bearing section 110 and a fixation section 120 that is coupled to the bearing section 110. The bearing section 110 may have the shape of an oval dome or a spherical dome. Referring to FIGS. 26A and 26B, it is illustrated that the bearing section 110 of the talar component 100 may be formed in the shape of an oval dome to have a medial-lateral radius MLR that is greater than a dorsal-plantar radius DPR relative to an axis, which may be a central axis CA as defined according to the present invention and is described further herein. If the bearing section 110 were to have equal radii, in contrast, the bearing section 110 would be in the shape of a spherical dome. It should be appreciated that these shapes are exemplary only, and may be adjusted as desired or necessary to account for patient-specific variables or otherwise. The fixation section 120 may include one or more fins 121 that will press-fit into a groove or other recess formed in the prepared talar site. The fin(s) 121 may have a rectangular cross-section with one or more beveled edges so the fin(s) 121 have at least one portion that decreases in width with an increase in distance from the bearing section 110. It should be appreciated that the fin(s) 121 may be integrally formed with the talar component 100 or, alternatively, may be reversibly coupled components that can be removed from the talar component 100 without damaging the talar component 100, allowing for the talar component 100 to have modular fixation elements. The fin(s) 121 may comprise, or be coated with, a porous ingrowth material that encourages tissue ingrowth into the fins 121 to provide stable fixation of the talar component 100 in the talus bone.

Referring specifically to FIGS. 3A-4 illustrating the navicular component 300, it can be seen that the navicular component 300 has a base 310 with an articulating section 320 coupled to the base 310. The base 310 may comprise titanium, as previously described, and include one or more fixation fins 311, illustrated as two fixation fins 311, that are similar to the fins 121 of the talar component 100 and may be reversibly coupled to the navicular component 300. The base 310 may have a curved surface 312, from which the fins 311 extend, and a flat surface 313 opposite the curved surface 312 that is coupled to the articulating section 320 having an articulation recess 322 formed therein. Following implantation, the bearing section 110 of the talar component 100 may rest within and articulate against the articulation recess 322, allowing articulation of the joint. FIGS. 5A-5D illustrate the talar component 100 and the navicular component 300 together forming the talonavicular joint prosthesis 500. The base 310 of the navicular component 300 may be 4 mm thick (top-to-bottom) while the articulation section 320 may have varying thicknesses of UHMWPE. The thickness of the UHMWPE of the articulation section 320 may be defined with respect to an interface surface 313A where the articulating section 320 has a greatest surface area interface with the base 310, with the thickness being between 3 mm at a minimum (between the interface surface 313A and a bottom of the articulation recess 322) and 11 mm at a maximum (between the interface surface 313A and a portion of the articulating section 320 that does not have the articulation recess 322 formed therein).

The talar component 100 and the navicular component 300 are shaped such that, when brought together, there is more conformity between the navicular component 300 and the talar component 100 in a dorsal-plantar plane than in a medial-lateral plane, as can be appreciated from FIGS. 5A-5D. As used herein, "conformity" generally refers to the degree in match between the shapes and dimensions of the talar component 100 and the navicular component 300. Conformity may be measured by measuring a volume in a particular region between the talar component 100 and the navicular component 300; the more volume that is present in the region, indicating a mismatch in the geometry, the less the conformity there is, and vice-versa. For example, the shape of the articulation recess 322 of the navicular component 300 and the bearing section 310 of the talar component 300 may be such that there is differing conformity along different axes. As can be appreciated from comparing FIG. 5D, which illustrates the components 100, 300 in the medial-lateral plane when brought together, and FIG. 5C, which illustrates the components 100, 300 in the dorsal-plantar plane when brought together, there is more conformity between the components 100, 300 in the dorsal-plantar plane (indicated by a smaller volume between the components 100, 300) than in the medial-lateral plane. To provide differing conformities, the articulation recess 322 and a bearing surface 111 of the bearing section 110 of the talar component 100 may be shaped so an articulation radius of curvature in the dorsal-plantar plane ARCDP of the articulation recess 322 and a bearing radius of curvature in the dorsal-plantar plane BRCDP of the bearing surface 111 are similar in a direction of a short axis of the natural talonavicular joint in order to support flexion and extension of the joint. In contrast, the articulation recess 322 and the bearing surface 111 of the bearing section 110 may be shaped so there is a mismatch between an articulation radius of curvature in the medial-lateral plane ARCML and a bearing radius of curvature in the medial-lateral plane BRCML in a direction of the long axis of the natural talonavicular joint. In this respect, the articulation radius of curvature in the medial-lateral plane ARCML of the articulation recess 322 may be greater than the bearing radius of curvature in the medial-lateral plane BRCML of the bearing surface 111 of the bearing section 110 of the talar component 100 to allow for translational movement between the components 100, 300 in the long axis. Additionally, along the long axis, the curvature of the short axis may be less conforming medially than laterally to allow for potential translation in all directions medially. In some embodiments, a ratio of the articulation radius of curvature ARCML to the bearing radius of curvature BRCML is between 1.25:1 and 2:1 in the medial-lateral plane (FIG. 5D) and/or a ratio of the articulation radius of curvature ARCDP to the bearing radius of curvature BRCDP is between 1:1 and 1.5:1 in the dorsal-plantar plane (FIG. 5C).

As can be appreciated from FIGS. 5C and 5D, the articulation recess 322 and the bearing surface 111 are symmetric in both the medial-lateral plane and the dorsal-plantar plane so the conformity between the components 100, 300 in both planes on one side of the formed prosthesis, e.g., a medial side, is the same as the conformity between the components 100, 300 in both planes on an opposite side, e.g., a lateral side. In some embodiments, the bearing surface 111 and the articulation recess 322 are shaped such that conformity between the components 100, 300 in the medial-lateral plane and the dorsal-plantar plane differs on a medial side of the prosthesis 500 compared to a lateral side of the formed prosthesis 500, i.e., the bearing surface 111 and the articulation recess 322 are asymmetric. For example, and referring now to FIG. 5E, a difference between a first articulation radius of curvature in the medial-lateral plane ARCML1 and the bearing radius of curvature in the medial-lateral plane BRCML may be greater on a medial side 326 of the formed prosthesis than the difference between a second articulation radius of curvature in the medial-lateral plan ARCML2 and the bearing radius of curvature in the medial-lateral plane BRCML on an opposite lateral side 327 of the formed prosthesis, i.e., the conformity between the components 100, 300 in the medial-lateral plane is less on the medial side 326 than the lateral side 327. Similarly, a difference between a first articulation radius of curvature in the dorsal-plantar plane and the bearing radius of curvature in the dorsal-plantar plane may be greater on the medial side 326 of the formed prosthesis than the difference between a second articulation radius of curvature in the dorsal-plantar plane and the bearing radius of curvature in the dorsal-plantar plane on the opposite lateral side 327 of the formed prosthesis, i.e., the conformity between the components 100, 300 in the dorsal-plantar plane is less on the medial side 326 than the lateral side 327. In such embodiments, the conformity between the components 100, 300 in the dorsal-plantar plane may still be greater than in the medial-lateral plane on the respective sides of the formed prosthesis. In some embodiments, the conformity between the components 100, 300 on the lateral side decreases at a non-constant rate in the medial-to-lateral direction. It should be appreciated that even though the articulation recess 322 is illustrated and described as having differing radii of curvature on the medial side 326 and the lateral side 327, in some embodiments the bearing surface 111 has differing radii of curvature on the medial side 326 and the lateral side 327 to provide different conformities, which may be alternatively to or in addition to the multiple radii of curvature of the articulation recess 322.

In accordance with the present invention, the talar and navicular components 100, 300 each have an inner (fixation) surface 114, 324 and an outer (articular) surface 111, 323 and a defined average thickness that quantifies the average distance between these component surfaces. Additionally, each component's inner surface 114, 324 is configured to generally follow the anatomic contour of the original joint surface to which each component 100, 300 is to be attached and to also minimize its average thickness consistent with providing sufficient strength and rigidity in the prosthesis' components, so as to yield minimum bone resection in the creation of the new prosthesis-accommodating joint space.

The outer surfaces 111, 323 are designed to articulate with each other to preserve motion of this joint and provide the ability to restore motion equivalent to the natural anatomy. The relationship of the mating outer surfaces 111, 323 is configured so that the radius of curvature is relatively conforming in the sagittal plane, to allow for dorsi-plantar flexion movement, and is less conforming in the coronal plane to allow for translation movement and/or adjust for misalignment of the implant axes relative to each other. Combined, these will allow for restoration of inversion and eversion of the foot.

Referring now to FIGS. 6A-7, exemplary embodiments of a talar component 700 and navicular components 600, 600A are illustrated that are modular. As can be seen, an articulating section 620 of the navicular component 600 may be formed with a section lip 621 and locking grooves 622 that are configured to accept and lock with one or more corresponding base lips 611 of a base 610. In some embodiments, the section lip 621 is flexible, e.g., formed of UHMWPE, while the base lip(s) 611 is rigid, e.g., formed of metal. The lips 611, 621 may be pressed together so the flexible section lip 621 flexes and snaps onto the base lip 611. As illustrated in FIGS. 6A and 6B, the flexible section lip 621 may be initially hooked onto the base lip 611 on a dorsal side before pushing down the articulating section 620 to snap the rest of the section lip 621 with the base lip 611 and lock the articulating section 620 to the base 610. It should be appreciated that the section lip 621 may alternatively be initially hooked onto the base lip 611 on the plantar side. In some embodiments, the flexible section lip(s) 621 may be solely located on the dorsal side of the articulating section 620. In some embodiments, the section lip(s) 621 are all flexible. In an alternative embodiment, and referring now to FIGS. 6E-6F, the base 610 is provided similarly to what is illustrated in FIGS. 6A-6B but an articulating section 620A is provided that has a flexible section lip 621A and a rigid section lip 621B. The flexible section lip 621A may be on a dorsal side of the articulating section 620 while the rigid section lip 621B may be on the plantar side of the articulating section 620A. The section lip 621A may be made flexible by making an undercut 622A adjacent to the section lip 621, which is not present adjacent to the rigid section lip 621B. The rigid section lip 621B has a configuration that allows the rigid section lip 621B to be inserted when the navicular component 600A is already implanted. The rigid section lip 621B engages the base lip 611 as the articulating section 620 is rotated onto the base 610. To facilitate insertion and rotation, the rigid section lip 621B may have angled surfaces 623 that correspond to surfaces of the base lip 611. An instrument 630, illustrated in FIG. 6C, may be used to further press the base lips 611 and the section lips 621, 621A, 621B together, locking the base 610 and the articulating section 620 together. As illustrated in FIG. 6D, the navicular component 600 may also include one or more slots 623 on the dorsal side that are shaped to accept an instrument, which may be the instrument 630 or a different instrument, allowing the instrument to grab hold of the talar component 700 to remove the talar component 700 from the navicular component 600.

The talar component 700 may be formed similarly by separating a bearing section 710 into two separable pieces 711, 712 that are held together by a press-fit or other interference fit. In some embodiments, there is no engagement between the material, such as UHMWPE, of the articulating section 620 and the base 610 on one or more sides of the articulating section 620. By forming the components 600, 600A, 700 as modular components, proper tension or restoration of the joint line can be achieved and/or one or both pieces can be replaced if there is damage to the components.

Referring now to FIGS. 8A and 8B, an exemplary embodiment of a patient specific guide 1200, which is illustrated in further detail in FIGS. 12-14, provided according to the present invention is illustrated. The guide 1200 is illustrated coupled to a talus bone and is configured such that a central axis CA within the talus is defined. The guide 1200 matches a dorsal surface DS of the talus and rigidly fixates hindfoot and midfoot bones in the proper orientation during bone preparation. The guide 1200 may be modular so the guide 1200 can be easily modified to prepare bones with differing degrees of deformity, as will be described further herein. In some embodiments, the talus is oriented at an angle α, such as 50°, that is off-axis to the coronal plane for resecting once the guide 1200 is fixated in the proper location and orientation.

The shape of the guide 1200 may be established based on imaging of the talus, as illustrated in FIGS. 9A and 9B, so the central axis CA is generally oriented perpendicular to an axis that extends through a length L of the talar head and/or parallel to an axis that extends through a width W of the talar head. An algorithm based off of either the navicular or the talar joint surface geometry may additionally, or alternatively, be used to determine the location of the central axis CA. As illustrated in FIG. 10, the guide 1200 can be used to define a perimeter P of the talar head and an area AR of the talar head. The area of the talar head is defined so an area adjacent to the perimeter P of the talus is excluded from bone preparation, in order to protect the surface of the talus below the exterior surface, and from articulation with the navicular component 300 following implantation. Once the guide 1200 is properly positioned, the central axis CA can be established in the talar bone using a mechanical element to guide the preparation of the bone surface. Utilizing the central axis CA to prepare the fixation surface in all planes helps to preserve bone. Cutting devices that can be used to prepare the bone surface may include, for examples, a mill 2300B that is curved in biplanar fashion (illustrated in FIG. 23B) to minimize the amount of bone removed and match the general curvature of the navicular or talar joint surface. The guide 1200 can be used in conjunction with a cutting mill to sweep the cutting mill along the curve in the long axis, with the mill 2300B being oval shaped and matching the curvature in the short axis.

Referring now to FIG. 11, a step that may be performed to prepare a navicular bone according to the present invention is illustrated, which may be performed via pre-operative planning in a view that is similar to what is illustrated in FIG. 9A. As can be seen, the location of a central axis CA can be established using a width for articulation $N_w$ of the navicular as well as a radius of curvature $R_N$ of the navicular bone in the dorsal view. To establish the central axis CA, the radius of curvature $R_N$ of the navicular bone and the width for articulation $N_w$ are measured. The radius of curvature $R_N$ is used to define two or more arcs, such as two arcs A1, A2, within the width for articulation $N_w$. The arcs A1, A2 may be, for example, respectively centered on a medial edge of articulation ME and a lateral edge of articulation LE, with the intersection defining a point P1 on the central axis CA. It should be appreciated that more than two arcs may be utilized, so long as the utilized arcs are on the radius of curvature $R_N$ and between the medial and lateral edges ME, LE of the width for articulation $N_w$. Once the central axis CA is established, the guide 800 may then be positioned so a central post of the guide 800 is aligned with the central axis CA. Milling and drilling of the bone may then be performed, using the guide 800 to guide formation of the holes and cuts. For preparation of navicular bone surfaces, 2-4 mm may be added to the radii of curvature $R_N$; for preparation of the talar surface, 4-8 mm may be subtracted from the radii of curvature $R_N$.

Referring now to FIGS. 12-14, the guide 1200 that may be provided and used according to the present invention is illustrated in further detail. As illustrated, the guide 1200 has been placed so an opening 1201 formed in the guide 1200 is aligned with a central axis CA of the navicular curvature, which may be determined as previously described, to assist a surgeon with preparing the site for the prosthesis. The guide 1200 may also have a plurality of additional openings 1202 that can act as guide openings for a drill or other cutting instrument, which may be used to cut the openings for fixation fins of the talar component. The guide 1200 may have one or more modular posts 1203 that are configured to attach to a cutting device guide and/or a cutting device, as will be described further herein, which may then be utilized to cut and/or mill the surface of the bone. Because the guide 1200 is positioned so the central axis CA of the navicular curvature is defined, the surface of the bone can be prepared in a manner that follows the natural curvature of the top surface of the bone and reduces the amount of healthy bone tissue that is resected in order to implant the prosthesis.

Referring now to FIGS. 15-17, an exemplary embodiment of a cutting guide assembly 1500 provided according to the present invention is illustrated that includes a cutting guide 1510 coupled to the modular posts 1203 of the guide 1200, which is aligned with the central axis CA as previously described in the context of FIGS. 12-14. The cutting guide 1510 has a cutting slot 1511 formed therein. The cutting guide 1510 may guide one or more cutting devices to cut into bone tissue. The guide 1200 is aligned with the central axis CA of the navicular curvature, as previously described, to properly orient the guide 1200 and the attached cutting guide 1510 (and any guided cutting devices) for preparation of the bones. The cutting guide 1510 is placed so the bone can be prepared without removing the plantar head, with cuts then being made using a cutting device inserted in the cutting slot 1511. In other words, the navicular bone and the talus bone can be prepared using at least one cutting device, and in some embodiments multiple cutting devices, and the cutting guide assembly 1500 to guide movement of the cutting device(s). Once the bones are prepared, the navicular component 300 can be placed in the prepared navicular bone and the talar component 100 can be placed in the prepared talus bone.

Referring now to FIGS. 18-21B, an exemplary embodiment and use of a drill guide assembly 1800 for preparing a talonavicular joint according to the present invention is illustrated. The drill guide assembly 1800 includes a drill guide 1810 coupled to the modular posts 1203 of the guide 1200, which is aligned with the central axis CA as previously described in the context of FIGS. 12-14. The drill guide 1810 has a plurality of drill openings 1811 formed therein. The drill guide assembly 1800 of FIGS. 18-21B has the opening 1201 of the guide 1200 aligned with a central axis CA of the navicular curvature, which may be established as previously described, to properly orient the drill guide 1810 for preparation of the bone. As can be seen, the drill guide 1810 has two series of drill openings 1811, with the drill openings 1811 of each series being aligned on a respective arc. A drill may be inserted into each of the openings 1811 to form one or two arcs of drill holes in the bone, as illustrated in FIGS. 21A and 21B, providing a template for cutting the bone. Once the drill holes are formed, a cutting device, such as a mill, may be moved along the series of drill holes to "connect the dots" and create the proper cut in the bone, as illustrated in FIG. 21B.

Referring now to FIGS. 22A and 22B, an exemplary embodiment of a cutting device assembly 2200 provided according to the present invention is illustrated that may be used in conjunction with the guide 1200 to connect drill holes formed in bone, e.g., connect the drill holes illustrated in FIGS. 21A and 21B using a cutting device, and/or otherwise prepare the joint for implantation of an implant. The cutting device assembly 2200 may be oriented so a central post 2201 of the cutting device assembly 2200 is aligned with the central axis CA, which may be established as previously described. The cutting device assembly 2200 may, for example, be placed so the central post 2201 is inserted in the opening 1201 of the guide 1200, which is aligned with the central axis CA. A first sleeve 2202 may be coupled to the central post 2201 and a rotatable arm 2203 may be coupled thereto in order to couple the first sleeve 2202 to a second sleeve 2204 that is configured to hold a cutting device, such as an orthopaedic mill 2210. The rotatable arm 2203 may rotate about the central post 2201, which may be aligned with the central axis CA, so the second sleeve 2204 and held cutting device 2210 also rotate about the central axis CA, allowing a user to rotate the orthopaedic mill 2210 along the formed drill holes of FIGS. 21A and 21B. The rotatable arm 2203 may be adjustable so a rotation radius R defined between the first sleeve 2202 and the second sleeve 2204 is adjustable, allowing the radius of the mill's 2210 movement to be adjusted. The rotation radius R may be adjusted, for example, by placing the rotatable arm 2203 in an arm slot formed in the first sleeve 2202 and displacing the rotatable arm 2203 within the arm slot. In some embodiments, the rotatable arm 2203 is graduated with distance lines to indicate the rotation radius R of the second sleeve 2204 and held cutting device 2210 relative to the first sleeve 2202.

Referring now to FIG. 22C, another exemplary embodiment of a cutting device assembly 2200C is illustrated that is similar to the cutting device assembly 2200 but includes one or more fixation arms, illustrated as a pair of fixation arms 2220. The fixation arms 2220 may be coupled to the central post 2201 and be configured to be fixated to a bone adjacent to the bone(s) being prepared, such as a cuneiform. Each fixation arm 2220 may have a fixation feature 2221 at its end 2222 that is configured to be fixated to bone. For example, the fixation feature 2221 may be an opening that is shaped and sized to accept a pin or other fixation element so the fixation feature 2221 is fixated to bone tissue. It should be appreciated that the fixation feature 2221 may also be configured to fixate directly into bone, e.g., by being a spike or similar construction. Fixating the fixation arm(s) 2220 to adjacent bone(s) can improve anchoring of the cutting device assembly 2200 during bone preparation to increase the reliability of cuts and reduce the risk of the cutting device 2210 moving in an undesired way during preparation.

In some exemplary embodiments provided according to the present invention, and referring further to FIGS. 23A-23B, a method of preparing a bone site and implanting the previously described talonavicular joint prosthesis 500 is provided. The method may include making a dorsal incision and retracting soft tissues around a natural talonavicular site TN. A central axis CA may be established. The central axis CA may be established from a radius of curvature $R_N$ using a guide, which may be a patient specific guide formed according to the present invention, to guide bone removal and preparation. A guide, such as the previously described guide 1200, may be aligned with the central axis CA such that the guide 1200 has at least a portion, such as an opening 1201, aligned with the central axis CA. The guide 1200 may couple to various other guides and/or instruments to prepare the bones, such as a surgical drill and various attachments/bits for the surgical drill. A cutting guide 1510 may be coupled to the guide 1200 to create an opening along the joint central axis CA in a dorsal view. The guide 1200 may be attached to the drill guide 1810 then the cutting device assembly 2200 to prepare the navicular bone by milling the navicular surface in the dorsal view to create medial-to-lateral curvature that minimizes the amount of navicular bone surface that is removed, as previously described in the context of FIGS. 18-22C. The talar surface may then be prepared by milling the talar bone using the cutting device assembly 2200, 2200C coupled to the guide 1200 in combination with the cutting device 2210, a cylindrical orthopaedic mill 2300A (FIG. 23A), and/or a curved (bi-planar) orthopaedic mill 2300B (FIG. 23B). Fixation element holes for the navicular component 300 and the talar component 100 are formed in the respective bones. Trial components for the navicular component 300 and the talar component 100 may be inserted in the formed fixation element holes to confirm proper placement and orientation. Articular surface trial components may also be inserted to establish the thickness of the polyethylene. Range of motion and stability may also be assessed using the trial components. The navicular component 300 may then be inserted so its fixation element(s), such as the fins 311, are properly located in their respective opening(s) in the prepared navicular bone and the talar component 100 may also be inserted so its fin(s) 121 are properly located in the respective opening(s) in the prepared talus bone. The UHMWPE insert of the navicular component 300, if the navicular component 300 is modular, may be inserted into the navicular component 300 and locked into place. The wound may then be closed.

In some instances, there is dorsal-plantar curvature in the navicular surface that can result in an undesirable amount of navicular bone being removed. In such an instance, an alternative approach may be used to prepare the joint for the prosthesis 500. The central axis CA may be established by defining at least two arcs A1, A2 from the radius of curvature $R_N$ within the width for articulation $N_w$ and defining a point P1 where the arcs A1, A2 intersect as being on the central axis CA, as previously described and illustrated in FIG. 11. At least a portion of the guide, such as an opening, is aligned with the established central axis CA. A drill is inserted at the central axis CA through the guide and the talus bone may be resected through the guide to create space. The drill is used as a center of rotation for drilling and milling of the bone about the central axis CA, which may be assisted using the various guides and guide assemblies 1510, 1810, 2200, 2200A described previously. A curved shaped mill 2300B, which is illustrated in FIG. 23B and may have a biplanar curve, is used to shape the navicular bone on a three-dimensional curved shape, which preserves the dorsal aspect of the navicular bone for support of the prosthesis 500. The milling design may be selected to match the navicular curvature that is measured.

In some embodiments, and referring now to FIG. 24, an additional wedge 2400 may be provided to address bone deficits, such as when there is a fracture or other type of significant damage to the talus bone and/or navicular bone. As illustrated, the wedge 2400 may be placed over an area of the bone deficit, shown in the navicular bone, and bear on the bone and an adjacent bone, such as a cuneiform, for stability. The adjacent bone may be fused to another adjacent bone, also illustrated as another cuneiform, to further stabilize the bones.

Referring now to FIGS. 25A-25C, another exemplary embodiment of a modular navicular component 2500 provided according to the present invention is illustrated. The navicular component 2500 includes a base 2510 removably coupled to an articulating section 2520 including an articulating surface 2521 with an articulation recess 2522. The articulating section 2520 is removably coupled to the base 2510 by a locking clip 2530, illustrated by itself in FIG. 25B, that fits in corresponding slots 2511, 2523 formed in the base 2510 and the articulating section 2520. The locking clip 2530 can be unclipped from the base 2510 and/or the articulating section 2520 to unlock the base 2510 and the articulating section 2520 from one another, allowing the base 2510 and the articulating section 2520 to be uncoupled.

From the foregoing, it should be appreciated that the talonavicular joint prosthesis 500 provided according to the present invention, and the method of implanting the prosthesis 500, provides a way to repair damaged talonavicular joints while minimizing the amount of removed healthy tissue and restoring the natural range of motion. The talar component 100 and the navicular component 300 of the prosthesis 500 are shaped so there is a high degree of conformity between the components 100, 300 in the dorsal-plantar plane to get a hinge effect that mimics the natural joint movement with less conformity in the medial-lateral plane so there is greater articulation in that plane. For preparing the bone, the previously described algorithm and method may be used to establish a central axis CA using the navicular radius of curvature $R_N$ and the intersection of arcs A1, A2 defined by the radius of curvature $R_N$. Patient specific guides and a central axis can be used for surface preparation and to establish the central axis of rotation for bone preparation. A guide and the central axis can be used to make deformity corrections for proper alignment of components and bone preparation of the talus and navicular surfaces while minimizing navicular bone resection in the medial-lateral and dorsal-plantar directions.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A talonavicular joint prosthesis, comprising:
a navicular component configured to be implanted in a navicular bone and comprising a base and a surface having an articulation recess formed therein, the articulation recess defining an articulation recess boundary within the surface; and
a talar component configured to be implanted in a talus bone and comprising a bearing section configured to rest within the articulation recess, the talar component and the navicular component being shaped such that, when brought together, there is more conformity between the navicular component and the talar component in a dorsal-plantar plane than in a medial-lateral plane, wherein there is separation between the bearing section and the articulation recess within the articulation recess boundary in both the dorsal-plantar plane and the medial-lateral plane when the talar component and the navicular component are brought together.

2. The talonavicular joint prosthesis of claim 1, wherein the bearing section comprises a bearing surface articulating against the articulation recess, the bearing surface defining a bearing radius of curvature and the articulation recess defining an articulation radius of curvature, wherein at least one of the following is satisfied:
the articulation radius of curvature is greater than the bearing radius of curvature;
a ratio of the articulation radius of curvature to the bearing radius of curvature is between 1.25:1 and 2:1 in the medial-lateral plane; or
a ratio of the articulation radius of curvature to the bearing radius of curvature is between 1:1 and 1.5:1 in the dorsal-plantar plane.

3. The talonavicular joint prosthesis of claim 1, wherein the bearing section has a medial-lateral radius that is greater than a dorsal-plantar radius relative to an axis extending through a geometric center of the bearing section.

4. The talonavicular joint prosthesis of claim 3, wherein the bearing section has the shape of an oval dome or a spherical dome.

5. The talonavicular joint prosthesis of claim 1, wherein the conformity between the talar component and the navicular component in at least one of the medial-lateral plane or the dorsal-plantar plane is greater on a lateral side of the talonavicular joint prosthesis than on a medial side of the talonavicular joint prosthesis.

6. The talonavicular joint prosthesis of claim 1, wherein the talar component or the navicular component is a modular component comprising a plurality of modular sections that removably couple together to form the modular component.

7. The talonavicular joint prosthesis of claim 6, wherein the modular component comprises an articulating section comprising the surface with the articulation recess formed therein, the articulating section being removably coupled to the base, wherein the base comprises base lips and the articulating section comprises section lips and locking grooves that are configured to accept and lock with the base lips.

8. The talonavicular joint prosthesis of claim 7, wherein at least one of the base lips or the section lips is a flexible lip located on a dorsal side of the articulating section.

9. The talonavicular joint prosthesis of claim 7, wherein the section lips are flexible and the base lips are rigid.

10. The talonavicular joint prosthesis of claim 9, wherein the sections lip are solely located on a dorsal side of the articulating section.

11. The talonavicular joint prosthesis of claim 9, wherein the section lips comprise ultra-high molecular weight polyethylene and the base lips comprise a metal.

12. The talonavicular joint prosthesis of claim 9, wherein the base lips and the section lips are configured to be pressed together so the section lips flex and snap onto the base lips.

13. The talonavicular joint prosthesis of claim 6, wherein the modular component comprises a locking clip that locks one of the modular sections to another one of the modular sections.

14. The talonavicular joint prosthesis of claim 1, wherein at least one of the following is satisfied:
the talar component comprises at least one fin configured to be inserted into a prepared talus bone; or the navicular component comprises at least one fixation fin configured to be inserted into a prepared navicular bone.

15. A talonavicular joint prosthesis, comprising:

a navicular component configured to be implanted in a navicular bone and comprising a base and a surface having an articulation recess formed therein; and a talar component configured to be implanted in a talus bone and comprising a bearing section configured to rest within the articulation recess, the talar component and the navicular component being shaped such that, when brought together, there is more conformity between the navicular component and the talar component in a dorsal-plantar plane than in a medial-lateral plane, wherein the bearing section has a medial-lateral radius that is greater than a dorsal-plantar radius relative to an axis extending through a geometric center of the bearing section.

16. The talonavicular joint prosthesis of claim 15, wherein the bearing section comprises a bearing surface articulating against the articulation recess, the bearing surface defining a bearing radius of curvature and the articulation recess defining an articulation radius of curvature, wherein at least one of the following is satisfied:

the articulation radius of curvature is greater than the bearing radius of curvature;

a ratio of the articulation radius of curvature to the bearing radius of curvature is between 1.25:1 and 2:1 in the medial-lateral plane; or a ratio of the articulation radius of curvature to the bearing radius of curvature is between 1:1 and 1.5:1 in the dorsal-plantar plane.

17. The talonavicular joint prosthesis of claim 15, wherein the talar component or the navicular component is a modular component comprising a plurality of modular sections that removably couple together to form the modular component.

18. The talonavicular joint prosthesis of claim 15, wherein the bearing section has the shape of an oval dome or a spherical dome.

19. The talonavicular joint prosthesis of claim 15, wherein the modular component comprises a locking clip that locks one of the modular sections to another one of the modular sections.

* * * * *